United States Patent [19]

Eickholt et al.

[11] 4,147,725

[45] Apr. 3, 1979

[54] PROCESS FOR PREPARING ANILINE COMPOUNDS FROM AMIDES WITH RHODIUM

[75] Inventors: Kathryn A. Eickholt, Midland; Robert H. Grubbs, East Lansing, both of Mich.

[73] Assignee: The Dow Chemical Company, Midland, Mich.

[21] Appl. No.: 888,892

[22] Filed: Mar. 22, 1978

[51] Int. Cl.$^2$ .......................... C07C 85/12; B01J 23/74
[52] U.S. Cl. ..................................... 260/578; 252/447; 252/472; 260/574; 260/575; 260/576; 260/577
[58] Field of Search ............... 260/578, 574, 575, 576, 260/577; 252/472, 447

[56] References Cited

U.S. PATENT DOCUMENTS 2,880,241  3/1959  Hughes ........................... 252/472 X
3,483,242  12/1969  Brownstein et al. ............ 260/578 X

OTHER PUBLICATIONS

Ginsburg, "Concerning Amines", First Ed., pp. 46-52, (1967).
Astle, "Industrial Organic Nitrogen Compounds", pp. 25-26, (1961).
Sidgwick, "Organic Chemistry of Nitrogen", Third Ed., pp. 100, 101 & 235, (1966).

Primary Examiner—Winston A. Douglas
Assistant Examiner—John Doll
Attorney, Agent, or Firm—G. R. Plotecher

[57] ABSTRACT

A vapor-phase process for preparing aniline or a substituted aniline, the process comprising contacting vaporous benzamide or a vaporous substituted benzamide with a metal catalyst, is improved by using rhodium as the metal catalyst.

9 Claims, No Drawings

PROCESS FOR PREPARING ANILINE COMPOUNDS FROM AMIDES WITH RHODIUM

BACKGROUND OF THE INVENTION

1. Field of the Invention:

This invention relates to the decarbonylation of benzamide compounds to aniline compounds.

2. Description of the Prior Art:

Mailhae, *Mem. Pres. Soc. Chem.*, 28, 9 (1925), teaches a vapor-phase decarbonylation of benzamide to aniline in the presence of metallic nickel. An aniline selectivity of 25 mole percent is reported but the teaching is silent as to benzamide conversion.

SUMMARY OF THE INVENTION

SUMMARY OF THE INVENTION

According to this invention, the vapor-phase process for preparing aniline or a substituted aniline, the process comprising contacting benzamide or a substituted benzamide with a metal catalyst, is improved when rhodium is used as the metal catalyst. Aniline selectivities in excess of 45 mole percent are achieved with a benzamide conversion in excess of 70 mole percent.

DETAILED DESCRIPTION OF THE INVENTION

Benzamide or a substituted benzamide is used in the practice of this invention. The substituted benzamides here used are of the formula

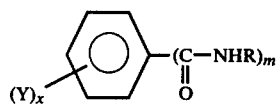
(I)

wherein R is hydrogen or methyl, Y is an inert-substituent, m is an integer of 1 or 2 and x is an integer of 0–3. By "inert-substituent" is meant a substituent that neither precludes the decarbonylation of (I) to aniline or a substituted aniline nor is significantly reactive with either the process reagents or products under the process conditions. Typical inert-substituents include $C_1$-$C_4$ alkyl and alkoxy, aryl, halogen, hydroxyl, carboxyl, etc. Y can also be carboxyl (—COOH) but this radical is typically eliminated from the benzene nucleus (via decarbonylation) during the practice of this invention, e.g., 4-carboxybenzamide (HOOC-$\phi$-CONH$_2$) produces aniline ($\phi$-NH$_2$). Exemplary noninert or active substituents are sulfur-containing moieties, nitro radicals and acyl radicals. When x is 2 or 3, each Y can be the same or different inert-substituents, e.g., where x is 2, each Y can be halogen or alkyl or one Y can be halogen while the other Y can be alkyl. When m is 2, each

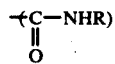

radical can be the same or different and such radicals can be ortho, meta or para to one another. Substituted benzamides where m is one and R is hydrogen are preferred to the other substituted benzamides and substituted benzamides wherein x is one and Y is $C_1$-$C_4$ alkyl are especially preferred. Exemplary substituted benzamides include p-hydroxybenzamide, monophthalamide, 2-methyl-m-phthaldiamide, 4-ethoxybenzamide, 4-phenylbenzamide, 3-chlorobenzamide, 3,5-dibromobenzamide, 3-methyl-5-chlorobenzamide, etc. Benzamide (I wherein x is 0, m is 1, and R is hydrogen) is most preferred.

Rhodium metal, usually finely divided and either supported or unsupported, is the catalyst of this invention. Fully reduced rhodium metal is preferred to partially reduced rhodium metal and supported rhodium metal is preferred to unsupported rhodium metal. The supports here used can vary to convenience and include such diverse materials as activated carbon, keiselguhr, pumice, aluminosilicates, etc. Activated carbon is the preferred support. The supports are loaded with a catalytic amount of rhodium. Typical supported catalysts consist of at least about one weight percent and preferably of about 2 weight percent rhodium. Practical considerations, such as convenience, economy, efficiency, etc., are the only maximum limitations upon the amount of rhodium that can be loaded upon a support but typically the maximum loading is about 15, and preferably about 10, weight percent rhodium.

The invention is practiced in the vapor phase. The process is typically conducted at a temperature between about 280° C. and about 500° C. and preferably between a temperature of about 350° C. and about 450° C. Most preferably, the process is conducted at a temperature between about 380° C. and about 425° C.

Although pressure is not critical to the practice of this invention and can thus be varied to convenience, best results are generally obtained under reduced pressure. Pressures between about 300 mm Hg and atmospheric are preferred. The benzamide or substituted benazmide is contacted with the rhodium metal catalyst for a sufficient period of time to allow decarbonylation. This contact or residence time will vary with the process reagents and conditions but a minimum contact time of about 5 seconds, and preferably of about 10 seconds, is generally employed. Contact times in excess of 100 seconds, and typically in excess of 60 seconds, are seldom necessary.

The process can be conducted in any known manner. For example, a stream of nitrogen or other inert gas carrier is bubbled through molten benzamide and carries benzamide vapor through a heated catalyst bed. Reaction products are then collected in a cold condenser and subsequently separated by any one of a number of standard techniques, such as distillation. Another suitable manner is to draw benzamide vapors from molten benzamide through a heated catalyst bed by the use of a slight vacuum. This process can be conducted in other manners as well.

Although the product of this improved process generally includes substantial amounts of benzonitrile or a substituted benzonitrile, this material can be easily hydrolyzed to the corresponding benzamide and thus recycled. In this manner of operation, the overall process efficiency is significantly increased.

The following example is an illustrative embodiment of this invention. Unless indicated to the contrary, all parts and percentages are by weight.

Specific Embodiment

Example:

A stream of nitrogen was bubbled through molten benzamide at a rate of about 120 cc/min. The nitrogen swept benzamide vapors at a pressure of ~300 mm Hg through a heated (~400° C.) catalyst bed consisting of 5 percent rhodium on activated carbon and then into a receiver. A dry-ice, cold finger condenser kept the products in the receiver and a dry-ice trap collected any volatiles. Gas chromatographic analysis showed the product to consist of 43 percent aniline, 51 percent benzonitrile and 6 percent benzoic acid. More than 70 percent of the benzamide was converted.

Controls A-C:

The above example was thrice repeated except that nickel, palladium and iridium were sequentially substituted for rhodium. The nickel control produced 2.5 percent aniline while the palladium and iridium controls produced no detectable aniline.

Although this invention has been described in considerable detail through the preceding example, it is to be understood that this example is for illustrative purposes only. Many variations and modifications can be made by one skilled in the art without departing from the spirit and scope of the invention.

What is claimed is:

1. An improved, vapor-phase process for preparing aniline or a substituted aniline, the process comprising contacting a compound of the formula

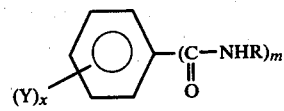

(I)

wherein R is hydrogen or methyl, Y is an inert-substituent, m is an integer of 1 or 2 and x is an integer of 0-3, with a metal catalyst, the improvement wherein the metal catalyst is rhodium.

2. The process of claim 1 wherein Y is selected from the group consisting of $C_1$-$C_4$ alkyl, alkoxy, aryl, halogen, hydroxyl and carboxyl.

3. The process of claim 2 wherein R is hydrogen and m is 1.

4. The process of claim 3 wherein Y is $C_1$—$C_4$ alkyl and x is 1.

5. The process of claim 1 wherein I is benzamide.

6. The process of claims 1, 2, 3, 4 or 5 wherein the contacting is conducted at a temperature between about 290° C. and about 500° C.

7. The process of claim 6 wherein the rhodium metal catalyst is loaded onto a suppport.

8. The process of claim 7 wherein the support is activated carbon.

9. The process of claim 8 wherein the supported catalyst consists of between about 2 and about 10 weight percent rhodium.

* * * * *